United States Patent [19]
Porter

[11] Patent Number: 5,897,832
[45] Date of Patent: Apr. 27, 1999

[54] CLEANING METHOD UTILIZING OZONATED WATER AND APPARATUS FOR PRODUCING OZONATED WATER

[76] Inventor: Brooks S. Porter, 381 Allen Ave., Wakefield, R.I. 02879

[21] Appl. No.: 08/640,241

[22] Filed: Apr. 30, 1996

[51] Int. Cl.⁶ ........................................ A61L 2/16
[52] U.S. Cl. .................. 422/28; 422/292; 422/44
[58] Field of Search ................... 422/23, 186.1, 422/44; 7/28, 29, 292, 305, 110, 106, 186.07; 604/4, 5, 6; 134/2, 22.19, 18, 26

[56] References Cited

U.S. PATENT DOCUMENTS

| | | | |
|---|---|---|---|
| 4,209,402 | 6/1980 | Gentles | 210/137 |
| 4,409,183 | 10/1983 | Fischer | 422/82.02 |
| 4,874,435 | 10/1989 | Caracciolo | 134/22.18 |
| 5,069,880 | 12/1991 | Karlson | 422/186.19 |
| 5,178,828 | 1/1993 | Uesugi | 422/22 |
| 5,207,237 | 5/1993 | Langford | 134/102.1 |
| 5,245,845 | 9/1993 | Langford | 68/355 |
| 5,256,371 | 10/1993 | Pippert | 422/28 |
| 5,266,275 | 11/1993 | Faddis | 422/116 |
| 5,268,144 | 12/1993 | Heilmann et al. | 422/26 |
| 5,336,165 | 8/1994 | Twardowski | 604/5 |
| 5,368,815 | 11/1994 | Kasting, Jr. et al. | 422/3 |
| 5,520,893 | 5/1996 | Kasting, Jr. et al. | 422/305 |
| 5,641,456 | 6/1997 | Rosenauer | 422/29 |

OTHER PUBLICATIONS

The Seratronics, Dialyzer Reprocessing System (Brochure), Nov. 1992.

Terumo Medical Corporation, Clirans Hollow Fiber Dialyzers (Brochure), Jan. 20, 1993.

*Primary Examiner*—E. Leigh McKane
*Assistant Examiner*—Alex Noguerola
*Attorney, Agent, or Firm*—Salter & Michaelson

[57] ABSTRACT

A method for cleaning an article, such as a used kidney dialyzer, requiring sterilization includes the steps of manually rinsing the article with purified water, inserting the article into an automated reuse apparatus which utilizes ozonated water, and sterilizing the article for a predetermined period of time with ozonated water wherein the ozonated water flows through the article for sterilizing it. The step of inserting the article into the automated reuse apparatus includes the steps of rinsing the article with ozonated water, reversing the flow of ozonated water through the article for backwashing the article, and conducting testing cycles wherein the article is tested for leaks therein and for ensuring it can contain a predetermined quantity of fluid. Preferably, the predetermined period of time of the sterilizing step is approximately thirty minutes. An apparatus for producing ozonated water is further disclosed.

4 Claims, 4 Drawing Sheets

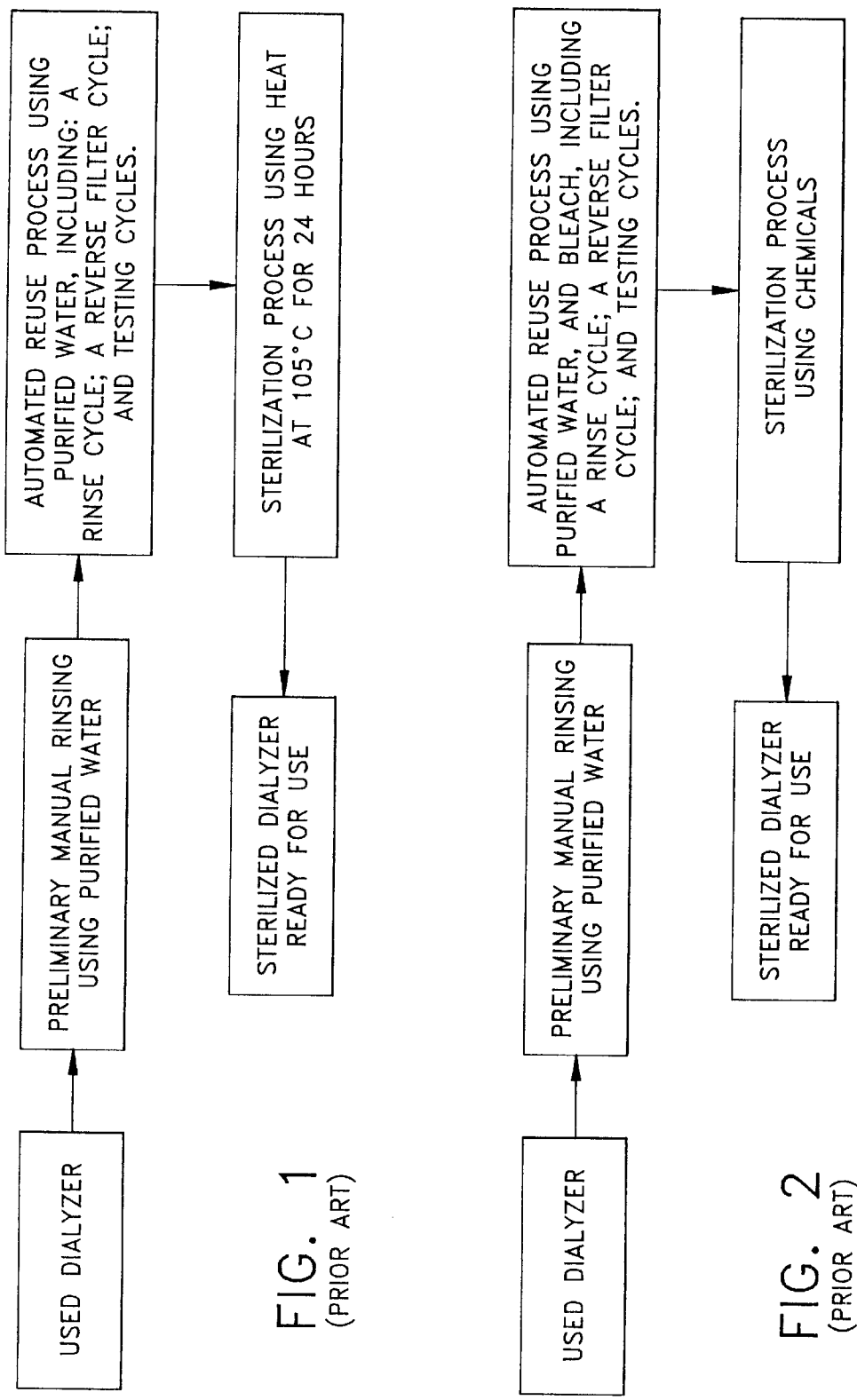

5,897,832

CLEANING METHOD UTILIZING OZONATED WATER AND APPARATUS FOR PRODUCING OZONATED WATER

BACKGROUND AND SUMMARY OF THE INVENTION

This invention relates generally to cleaning methods, and more particularly to a novel cleaning method for sterilizing an artificial kidney (i.e., a kidney dialyzer) with ozonated water. This invention also relates to an apparatus for producing ozonated water used during the performance of the cleaning method.

Disposable artificial kidneys have been reprocessed and reused in chronic hemodialysis for more than twenty years. Reuse of artificial kidneys has clearly become a standard medical practice in the United States, wherein over seventy percent of dialysis facilities are reusing artificial kidneys. These facilities treat over seventy percent of the dialysis patients in the United States.

Other than by hand washing the artificial kidney or dialyzer, there are two well-known methods for sterilizing the dialyzer. One such method, as shown in FIG. 1, is a method utilizing heat to clean the dialyzer. More specifically, the dialyzer is subjected to manual rinsing using purified water. The dialyzer then is rinsed with purified water, reverse filtered (also with purified water) and tested in an automated reuse apparatus which is well-known in the art. The dialyzer is then subjected to 105 degrees Celsius for a period of twenty-four hours for sterilization purposes. A disadvantage of this method is that it takes too long to complete, especially for hospitals, and other medical facilities, having many patients requiring dialysis. Another disadvantage is that the dialyzer does not tolerate being subjected to high temperatures very well (e.g., the dialyzer becomes cracked, or it may melt) which results in fewer reuses thereof.

The other known method follows the same prescribed method as heat treating, except instead of subjecting the dialyzer to heat over a period of time, suitable chemicals are used to sterilize it. This method is disclosed in FIG. 2. Various chemicals or sterilizing agents which are presently used are: cidex®; diacide®; sporicidin®-hd; formaldehyde; renalin®; and peracetic acid. While taking less time than heat treating (approximately two and one half hours), one problem associated with using chemicals is that there is a risk that the chemicals may remain inside the dialyzer and pose a threat to the patient during subsequent use of the dialyzer. Another drawback is that the chemicals are difficult to dispose of after they have been used. Moreover, many of the aforementioned chemicals are very expensive.

Ozone has been used as a sterilizing agent in the past. For example, in U.S. Pat. No. 5,266,275 to Faddis, there is disclosed a method and apparatus for sterilizing medical instruments using ozone. However, ozone has never heretofore been used to sterilize a used dialyzer.

Thus, there is presently a need for a method of sterilizing a used dialyzer which is not time-consuming and which leaves the dialyzer free of chemicals and other contaminants.

The present invention is directed to a method for cleaning an article, such as a used kidney dialyzer, requiring sterilization comprising the steps of: (a) manually rinsing the article with purified water; (b) inserting the article into an automated reuse apparatus which utilizes ozonated water; and (c) sterilizing the article for a predetermined period of time with ozonated water, the ozonated water flowing through the article for sterilizing it. More specifically, the step of inserting the article into the automated reuse apparatus comprises the steps of: rinsing the article with ozonated water; reversing the flow of ozonated water through the article for backwashing the article; and conducting testing cycles wherein the article is tested for leaks therein and for ensuring it can contain a predetermined quantity of fluid. Preferably, the predetermined period of time of the sterilizing step is approximately thirty minutes.

An apparatus for producing ozonated water of the present invention comprises a container defining a chamber. The container has a first inlet for introducing purified water into the chamber, a second inlet for introducing vaporized ozone into the chamber, and an outlet for venting ozonated water from the chamber. A pump siphons ozonated water from the chamber of the container via the outlet of the container. Suitable introducing means is provided for introducing vaporized ozone into the chamber of the container through the second inlet. A sensor measures oxygen reduction potential (ORP) of the ozonated water, and controls the amount of vaporized ozone introduced into the chamber of the container by the introducing means.

The introducing means of the apparatus specifically comprises a venturi injector in fluid communication with the second inlet of the container for injecting vaporized ozone therein. A device is provided for manufacturing oxygen, and an ozone generator, in fluid communication with the device and with the venturi injector, creates ozone which is then delivered to the venturi injector. A level control regulates the level of ozonated water contained within the chamber by introducing purified water therein when the level of ozonated water is below a predetermined quantity. Moreover, a filter is in fluid communication with the chamber of the container for further filtering and purifying the ozonated water contained within the chamber of the container.

Accordingly, among the several objects of the present invention are the provision of an improved method for cleaning a used dialyzer requiring sterilization which requires less time than other known methods; the provision of such an improved method which leaves the dialyzer completely clean without substantially any residue from chemicals or other contaminants being left thereon which present a potential risk to the patient and to employees handling the dialyzer; the provision of such a method which is a cost-effective alternative to known prior methods of sterilization; the provision of such a method which is capable of utilizing existing cleaning equipment; the provision of such a method which enables the dialyzer to be used immediately after completion of the cleaning method; and the provision of such a method which is easy to perform, simple to implement, and which little or no specialized training is required for persons conducting the method.

Also among the several objects of the present invention are the provision of an apparatus for producing ozonated water which is compact in construction and can deliver ozonated water to a device requiring the same on site; the provision of such an apparatus which produces sterilized ozonated water suitable for medical use; and the provision of such an apparatus which is easy to operate, simple in construction, and cost-efficient to manufacture and operate.

Other objects, features and advantages of the invention shall become apparent as the description thereof proceeds when considered in connection with the accompanying illustrative drawings.

BRIEF DESCRIPTION OF THE DRAWINGS

In the drawings which illustrate the best mode presently contemplated for carrying out the present invention:

FIG. 1 is a flow chart illustrating a known method of sterilizing articles, such as a used kidney dialyzer, which utilizes heat;

FIG. 2 is a flow chart illustrating another known method of sterilizing articles which utilizes chemicals;

Corresponding reference numerals designate corresponding parts throughout the several views of the drawings.

DETAILED DESCRIPTION OF THE PREFERRED EMBODIMENT

Figure 3:
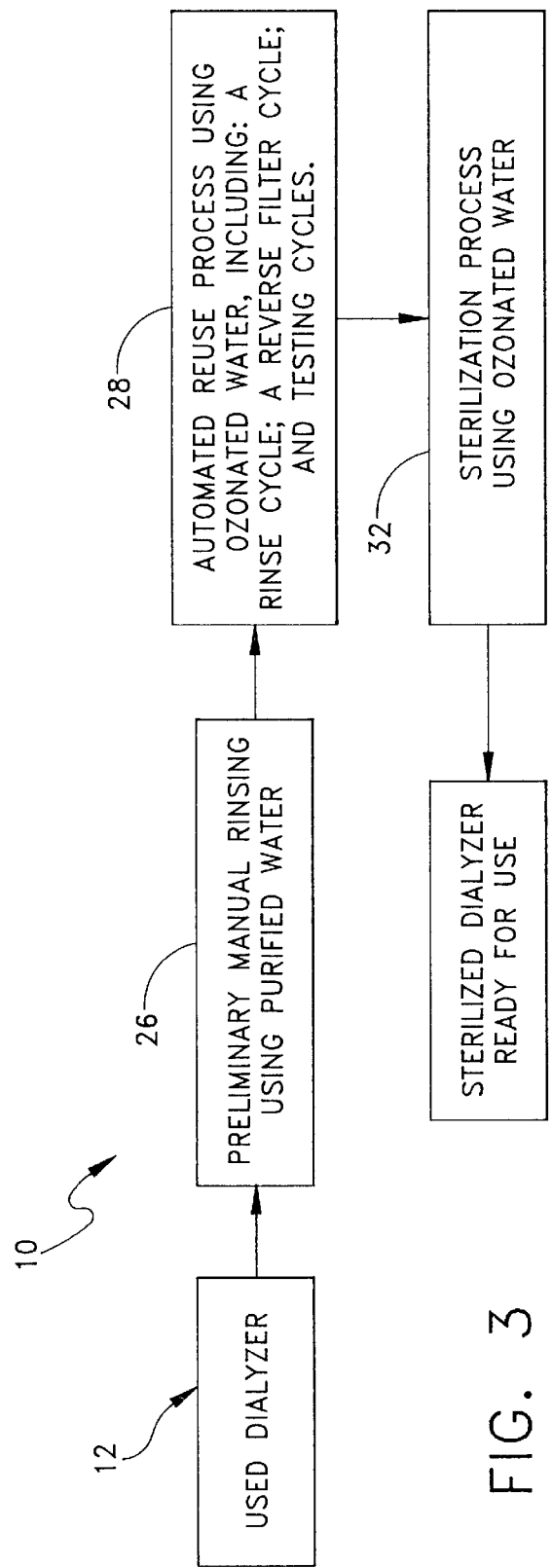
FIG. 3 is a flow chart illustrating a method of the present invention for sterilizing articles which utilizes ozonated water.
Figure 4:
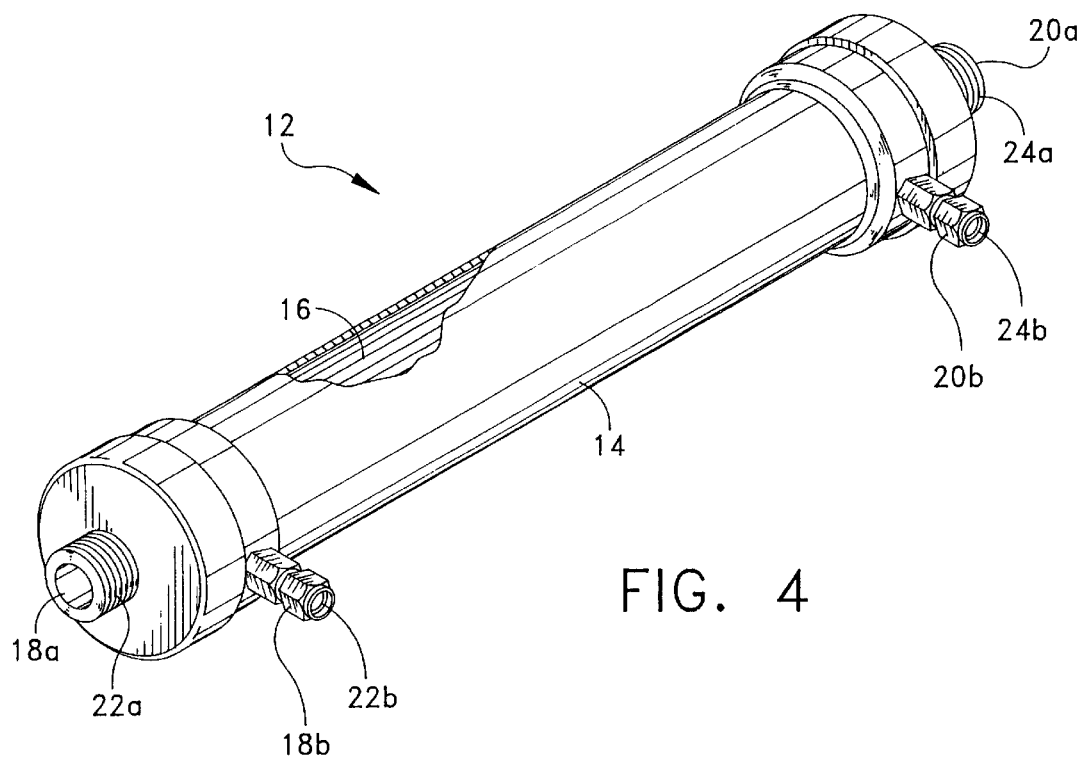
FIG. 4 is a perspective view of a kidney dialyzer constructed in the typical manner.

Referring now to the drawings, and more particularly to FIGS. 3 and 4, there is generally designated 10 a method of the present invention (see FIG. 3) for cleaning an article, such as a used kidney dialyzer, generally designated 12 (see FIG. 4), requiring sterilization. The method 10 of the present invention is directed to using ozonated water for sterilizing the dialyzer 12. It has been discovered that ozonated water quickly and efficiently cleans the dialyzer 12 without having to resort to using a temperature cleaning apparatus or to treating the dialyzer with chemicals.

Referring to FIG. 4, the blood dialyzer 12 is constructed in a typical fashion to include a tubular body 14 having an interior region 16 filled with a suitable filtration medium (e.g., fibers) which filter the person's blood of harmful toxins in the well-known manner. The interior region 16 is accessed through a first inlet 18a and a first outlet 20a provided at opposite open ends of the body 14 of the dialyzer 12 for introducing into and exhausting the patient's blood from the dialyzer 12. A second inlet 18b and a second outlet 20b are provided for introducing and exhausting dialyzing fluids into the dialyzer 12. Suitable connectors 22a, 22b, 24a, 24b (e.g., threaded formations) are located at the inlets 18 and outlets 20, respectively, so as to enable the dialyzer 12 to be coupled with feed and discharge conduits when treating a patient. An example of such a dialyzer is that sold by Terumo® of Somerset, N.J., under the trademark Clirans®. Since many of the presently available blood filtration devices can be used more than once, a used dialyzer must be thoroughly cleaned so that it is sterile for reuse. As mentioned above, there are known methods of sterilizing the used dialyzer, but each suffers from one or more noted disadvantages. The present method 10 is superior to that of these known methods in that it can be performed at a reduced cost, has a quick turnaround time, and more importantly does not present a risk to the patient reusing the dialyzer 12 by subjecting the patient to harmful chemical residue remaining inside the filtration medium of the dialyzer.

As illustrated in FIG. 3, the used dialyzer 12 is first manually rinsed using purified water. This preliminary step is designated by reference numeral 26 in FIG. 3. It should be noted that purified water flows through the inlets 18 of the used dialyzer 12, through the interior region 16 having the filtration medium, and out of its outlets 20. The water is purified by using well-known methods for sterilizing water used for medical purposes. For example, the water can be treated by using a distilling process, a deionizing process, or a reverse osmosis process, each of these processes being adapted to eliminate aluminum, fluorides, and sulfates, for example, from the water.

Once the used dialyzer 12 is preliminarily rinsed, it is then placed into an automated reuse apparatus, such as a dialyzer reprocessing apparatus sold by Seratronics Inc. of Walnut Creek, Calif., model nos. DRS4™D and DRS4™ND, for a more thorough cleaning. This step of the process and the apparatus itself are indicated by reference numeral 28 in FIG. 3. The reuse apparatus 28 has suitable connectors which mate with the connectors 22a, 22b, 24a, 24b of the dialyzer 12 for coupling the dialyzer to the reuse apparatus. Thus, it should be observed that the dialyzer 12 is adapted to be in fluid communication with the reuse apparatus 28 so that it can deliver ozonated water thereto for cleaning the dialyzer. The apparatus 28 is capable of delivering ozonated water into the interior region 16 of the dialyzer 12 through its inlet 18 for sterilizing the filtration medium.

More specifically, the apparatus 28 rinses the dialyzer 12 with ozonated water for a limited time period. Once rinsed with ozonated water, the flow of the ozonated water is reversed for backwashing the dialyzer 12. Ozonated water is suitably delivered to the reuse apparatus 28 from an apparatus for producing ozonated water which is generally designated at 30 in FIG. 5.

Next, the reuse apparatus 28 conducts a series of testing cycles on the dialyzer 12. One testing cycle includes testing for leaks in the dialyzer 12 wherein pressurized fluid is supplied within the dialyzer. Leaks formed by cracks or unsecured fittings are detected by the apparatus 28 in any suitable manner. Another testing cycle includes testing for whether the dialyzer 12 is capable of containing a predetermined amount of fluid. It is important that the dialyzer be able to contain a predetermined amount of fluid (e.g., 80% of a quart). Such tests are well-known in the art of reuse apparatus.

After conducting the rinsing cycle, backwashing cycle, is and testing cycle, ozonated water is then passed through the dialyzer 12 for a predetermined period of time. This step of the method is indicated by reference numeral 32 in FIG. 3. As mentioned above, the reuse apparatus 28 is connected to the apparatus 30 which produces ozonated water. Preferably, the dialyzer 12 is sterilized for a period of approximately thirty minutes. It has been discovered that thirty minutes is a sufficient amount of time for adequately sterilizing the dialyzer 12 whereupon, afterwards, it is ready for reuse.

It should be observed that the method 10 of the present invention is superior to the known methods illustrated in FIGS. 1 and 2 of the prior art. For example, using ozonated water reduces the amount of time necessary to sterilize the used dialyzer 12. Heat treating requires twenty-four hours and chemical treating requires two and one-half hours, whereas the method 10 of the present invention requires only one hour total. This reduction in time enables the health care facility to reduce the number of artificial kidneys for treating patients requiring dialysis since the artificial kidneys can be quickly cleaned for reuse. Also, since ozonated water is not particularly harmful, any residue thereof on the dialyzer 12 is not harmful to the patient. In sharp contrast, chemicals left on the dialyzer as a result of chemical treating can potentially be very harmful to the patient.

Figure 5:
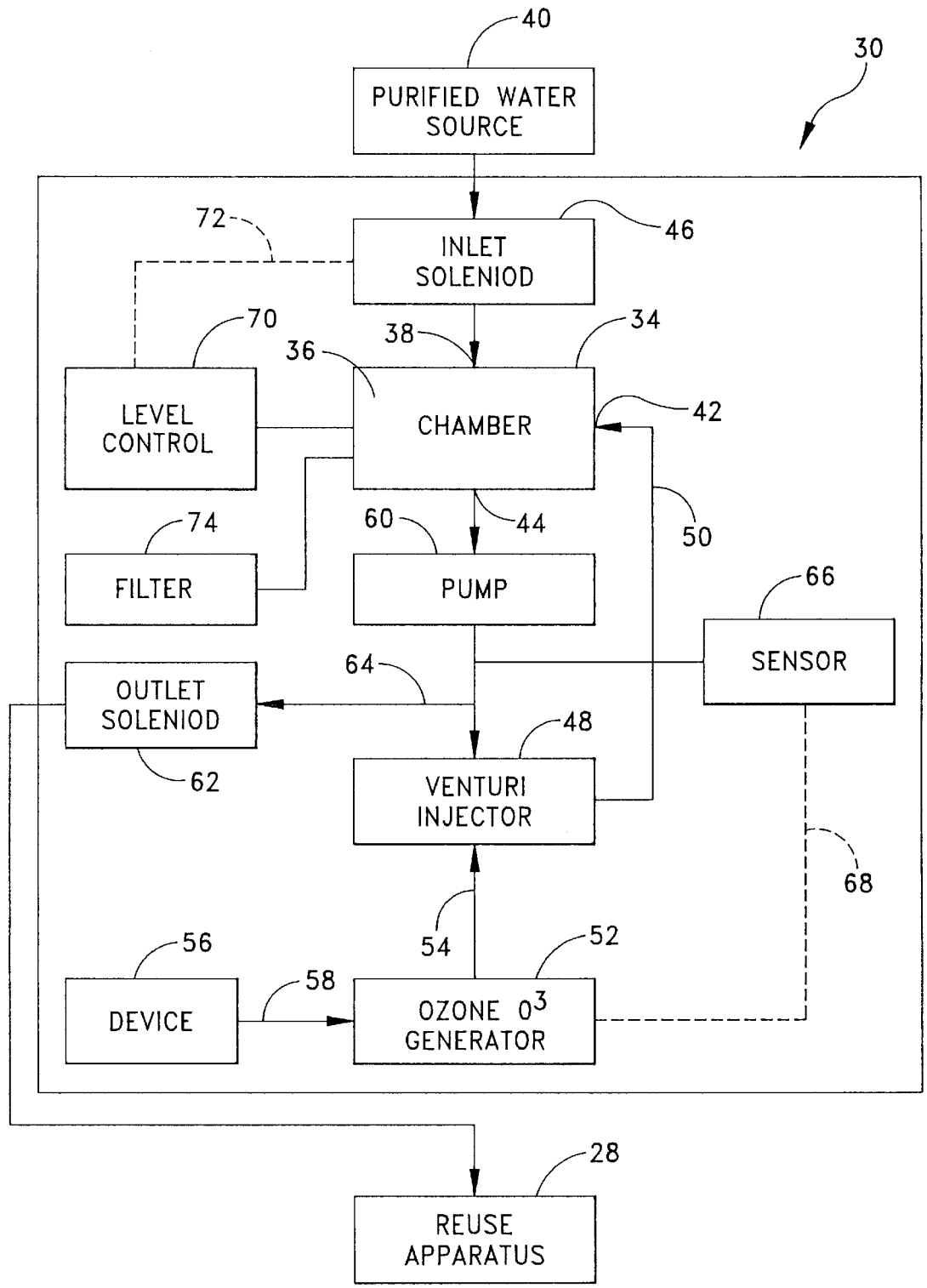
FIG. 5 is a schematic block diagram illustrating an apparatus of the present invention for producing ozonated water.

Referring now to FIG. 5, there is illustrated in schematic format a block diagram of the apparatus 30 for producing ozonated water. As mentioned briefly above, ozonated water is produced on-site by apparatus 30 and is delivered directly to the reuse apparatus 28 for sterilizing the dialyzer 12. The ozonated water producing apparatus 30 generates ozonated water at a rate sufficient for the reuse apparatus 28 to operate. As shown, the apparatus 30 comprises a container 34 which defines an inner chamber 36 wherein purified water is mixed with ozone ($O_3$) to produce the ozonated water. The container 34 has a first inlet 38 for introducing purified water from a purified water source 40 into the chamber 36, a second inlet 42 for introducing vaporized ozone into the chamber, and an outlet 44 for exhausting ozonated water from the chamber. An inlet solenoid 46 is disposed between the purified water source 40 and the chamber 36 for controlling the introduction of purified water into the chamber.

Ozone is injected into the chamber 36 of the container 34 through the second inlet 42 by a venturi injector indicated by reference numeral 48 in FIG. 5. The venturi injector 48 is in fluid communication with the chamber 36 of the container 34 via line 50, and in fluid communication with a ozone generator 52 via line 54, the ozone generator 52 creating ozone which is delivered to the venturi injector 48. An oxygen producing device 56 is in fluid communication with the ozone generator 52 by another line 58. The arrangement is such that the device 56 produces oxygen that is delivered to the ozone generator 52 which in turn creates ozone therefrom. This ozone is then vaporized by the venturi injector 48 and delivered to the container 34 by line 50 where it is mixed with the purified water to produce ozonated water. It should be noted that the venturi injector 48, ozone generator 52 and oxygen producing device 56 are all stock items that can be readily obtained through commercial channels.

The ozonated water produced in the chamber 36 of the container 34 is preferably saturated with ozone for obtaining the highest level of sanitation when cleaning the dialyzer 12 pursuant to the method 10 disclosed herein. The ozonated water is then delivered to the reuse apparatus 28 by a pump 60 which is in fluid communication with an outlet solenoid 62 via line 64. Excess ozone (unsaturated) which does not mix with the purified water is delivered back into the venturi injector 48 for atomization and reintroduction into the chamber 36. Thus, it should be observed that the apparatus 30 of the present invention conserves ozone and ensures that it is not wasted or otherwise released into the environment.

A sensor 66 measures the oxygen reduction potential (ORP) of the ozonated water for ensuring the ozonated water is saturated with ozone. This sensor 66 is in fluid communication with line 64 between the pump 60 and the venturi injector 48 and the outlet solenoid 62, and in electrical communication with the ozone generator 52 by line 68. The sensor 66 controls the amount of vaporized ozone introduced into the chamber 36 of the container 34 by the venturi injector 48 wherein it increases the amount of vaporized water delivered to the chamber when the ORP is below a predetermined level (e.g., 900 MV) and vice versa.

A level control 70 is provided within the chamber 36 of the container 34 for regulating the level of ozonated water contained therein by introducing more purified water into the chamber when the level of ozonated water is below a predetermined quantity. The level control 70 is in electrical communication with the inlet solenoid 46 via electrical line 72. A filter 74 is also in fluid communication with the chamber 36 of the container 34 for further filtering and purifying the ozonated water. The filter 74 further ensures that the ozonated water within the chamber 36 is pure and sterile when it is delivered to the reuse apparatus 28. As with the other aforementioned components of the apparatus 30, the level control 70 and filter 74 are also stock items readily available from commercial sources.

The operation of the ozonated water producing apparatus 30 is as follows. Purified water is delivered into the chamber 36 of the container 34 by the inlet solenoid 46 from source 40. The level control 70 regulates the amount or rate of purified water delivered to the chamber 36. Ozone vapor is delivered into the chamber 36 by the venturi injector 48, the ozone being mixed with the purified water for creating ozonated water within the chamber. The sensor 66 controls the amount of ozone which is delivered into the chamber 36 by sensing the ORP value of the ozonated water. The ozonated water is filtered by filter 74 and then pumped to the reuse apparatus 28 by the pump 60. The outlet solenoid 62 controls the amount of ozonated water which is delivered to the reuse apparatus 28. It should be observed that a suitable microprocessor is provided for controlling the operation of the apparatus 30 so that ozonated water having the requisite ORP value is delivered to the reuse apparatus 28 upon demand.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A method for preparing a kidney dialyzer for reuse, the kidney dialyzer having an interior region, an input and an output, the method comprising the steps of:
   (a) performing a preliminary rinse phase by rinsing the kidney dialyzer with purified water;
   (b) performing a secondary rinse phase, said secondary rinse phase comprising:
      (1) rinsing the kidney dialyzer with ozonated water by flowing said ozonated water from said input, through said interior region, to said output for a first amount of time; and
      (2) rinsing said kidney dialyzer with ozonated water by flowing said ozonated water from said output, through said interior region, to said input for a second amount of time;
   (c) performing a test phase by pressurizing said interior region to determine the presence of leaks in said kidney dialyzer; and
   (d) sterilizing said kidney dialyzer by flowing ozonated water through said kidney dialyzer for a third amount of time, the third amount of time being greater than said first and second amounts of time.

2. The method of claim 1, wherein said test phase further comprises filling said kidney dialyzer with a fluid to determine a volume of said kidney dialyzer.

3. A method for sterilizing a kidney dialyzer having an interior region, an input and an output, the method comprising the steps of:

(a) performing a preliminary rinse phase by rinsing the kidney dialyzer with purified water;

(b) performing a secondary rinse phase, said secondary rinse phase comprising:

(1) rinsing the kidney dialyzer with ozonated water by flowing said ozonated water from said input, through said interior region, to said output for a first amount of time; and (2) rinsing said kidney dialyzer with ozonated water by flowing said ozonated water from said output, through said interior region, to said input for a second amount of time;

(c) performing a test phase by filling said kidney dialyzer with a fluid to determine a volume of said kidney dialyzer; and (d) sterilizing said kidney dialyzer by flowing ozonated water through said kidney dialyzer for a third amount of time, the third amount of time being greater than said first and second amounts of time.

4. The method of claim 3, wherein said test phase further comprises pressurizing said interior region to determine the presence of leaks in said kidney dialyzer.

* * * * *